United States Patent
DoBrava et al.

(10) Patent No.: US 7,189,250 B2
(45) Date of Patent: Mar. 13, 2007

(54) ASPIRATING BALLOON CATHETER FOR TREATING VULNERABLE PLAQUE

(75) Inventors: Eric M. DoBrava, Crystal, MN (US); Jaydeep Y. Kokate, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 199 days.

(21) Appl. No.: 10/044,277

(22) Filed: Jan. 10, 2002

(65) Prior Publication Data

US 2003/0130672 A1    Jul. 10, 2003

(51) Int. Cl.
    *A61M 29/00*    (2006.01)
(52) U.S. Cl. ..................... 606/194; 604/96.01
(58) Field of Classification Search ............... 606/159, 606/192, 194, 198, 200; 604/534, 535, 536, 604/96, 101, 101.05, 96.01
    See application file for complete search history.

(56) References Cited

U.S. PATENT DOCUMENTS

| | | |
|---|---|---|
| 4,690,672 A | 9/1987 | Veltrup |
| 4,717,379 A | 1/1988 | Ekholmer |
| 4,921,476 A | 5/1990 | Wuchinich |
| 5,011,488 A | 4/1991 | Ginsburg |
| 5,037,431 A | 8/1991 | Summers et al. |
| 5,084,013 A | 1/1992 | Takase |
| 5,318,518 A | 6/1994 | Plechinger et al. |
| 5,370,609 A | 12/1994 | Drasler et al. |
| 5,527,292 A * | 6/1996 | Adams et al. ............... 604/171 |
| 5,688,234 A | 11/1997 | Frisbie |
| 5,749,858 A | 5/1998 | Cramer |
| 5,795,331 A | 8/1998 | Cragg et al. |
| 5,827,229 A | 10/1998 | Auth et al. |
| 5,833,650 A * | 11/1998 | Imran .......................... 604/509 |
| 5,879,361 A * | 3/1999 | Nash .......................... 606/159 |
| 5,891,111 A | 4/1999 | Ismael |
| 5,916,192 A | 6/1999 | Nita et al. |
| 5,947,985 A * | 9/1999 | Imran .......................... 606/159 |
| 5,989,271 A | 11/1999 | Bonnette et al. |
| 6,022,336 A * | 2/2000 | Zadno-Azizi et al. ... 604/101.05 |
| 6,231,588 B1 * | 5/2001 | Zadno-Azizi ............... 606/200 |
| 6,234,995 B1 * | 5/2001 | Peacock, III ............. 604/96.01 |
| 6,287,320 B1 * | 9/2001 | Slepian ....................... 606/194 |
| 6,511,503 B1 * | 1/2003 | Burkett et al. ............. 623/1.11 |
| 6,605,084 B2 * | 8/2003 | Acker et al. .................. 606/28 |

FOREIGN PATENT DOCUMENTS

| WO | WO 98/39047 | 9/1998 |
|---|---|---|
| WO | WO 00/69323 | 11/2000 |

* cited by examiner

*Primary Examiner*—Michael J. Hayes
*Assistant Examiner*—Victor Nguyen
(74) *Attorney, Agent, or Firm*—Fish & Richardson P.C.

(57) ABSTRACT

Devices and methods for extracting core material contained in plaque deposits inside a blood vessel are presented. A device in accordance with one embodiment of the invention includes a catheter having an elongate shaft, a collection array of a plurality of collection lumens disposed about the distal portion of the elongate shaft, a means for radially extending and/or collapsing the collection array, and a suction means for extracting material from the lumen of the blood vessel. A method in accordance with one embodiment of the present invention includes the steps of inserting the distal portion of the catheter into a lumen of the blood vessel, positioning the distal end of the collection array proximate plaque deposits, extending the collection array to rupture the plaque deposits and urging core material therefrom, and extracting the material using a suction means fluidly coupled to the proximal end of the collection array.

20 Claims, 5 Drawing Sheets

ASPIRATING BALLOON CATHETER FOR TREATING VULNERABLE PLAQUE

FIELD OF THE INVENTION

The present invention relates generally to intravascular catheters. More particularly, the present invention relates to intravascular catheters adapted to remove vulnerable plaque.

BACKGROUND OF THE INVENTION

Atherosclerotic coronary artery disease is a leading cause of death in industrialized countries. An atherosclerotic plaque is a thickening in the wall of the artery. Typically, patients who die of coronary disease may have several atherosclerotic plaques; however, in most instances of myocardial infarction, cardiac arrest, or stroke, it is found that only one of these potential obstructions had, in fact, ruptured, fissured, or ulcerated. The rupture, fissure, or ulcer typically causes a large thrombus to form on the inside of the artery, which may completely occlude the flow of blood through the artery, thereby injuring the heart and/or the brain.

Plaque, a thickening in the arterial vessel wall results from the accumulation of cholesterol, proliferation of smooth muscle cells, secretion of a collagenous extracellular matrix by the cells, and accumulation of macrophages and eventually, hemorrhage (bleeding), thrombosis (clotting), and calcification. The consensus theory is that atherosclerotic plaque develops as a result of irritation or biochemical damage to the endothelial cells which line the inner surface of the blood vessel. Endothelial cells normally prevent inappropriate formation of blood clots and inhibit contraction and proliferation of the underlying smooth muscle cells. Most investigators believe that atherosclerotic plaques can develop when endothelial cells are damaged or dysfunctional. Dysfunctional endothelial cells typically result from cigarette smoking, high serum cholesterol (especially oxidized low density lipoprotein), hemodynamic alterations (such as those found at vessel branch points), some viruses (herpessimplex, cytomegalovirus) or bacteria (e.g., chlamydia), hypertension, some hormonal factors in the plasma, and other factors as yet unknown. As a result of these gradual injuries to the endothelial cells, an atherosclerotic plaque may grow slowly over many years.

When a plaque rupture develops, there is typically a hemorrhage into the plaque through a fissure where the surface of the plaque meets the bloodstream. A thrombus quickly forms upon contact with the collagen and lipid of the plaque. This blood clot may then grow to completely occlude the vessel, or it may remain only partly occlusive. In the latter case, the new clot quite commonly becomes incorporated into the wall of the plaque, creating a larger plaque.

The condition of plaque deposits can vary. For example, the plaque can be inflamed and unstable, or the plaque can be quite stable. Plaque deposits that are at risk of rupturing are sometimes referred to as vulnerable plaque. Vulnerable plaque typically include a core of soft material covered with a fibrous cap. Many of vulnerable plaque deposits do not limit the flow of blood through the blood vessels. It has recently been appreciated that vulnerable plaques that do not limit flow may be particularly dangerous because they produce no warning symptoms, and can suddenly rupture causing heart attack, stroke, and/or death by forming a blood clot inside the blood vessel lumen and causing a blockage, for example.

SUMMARY OF THE INVENTION

A device in accordance with an embodiment of the present invention is a catheter including an elongated shaft with a collection array having a plurality of collection lumens disposed about a portion of the elongated shaft proximate the distal end of the elongated shaft. Each collection lumen could be defined by a first circumferential wall, a second circumferential wall, a first radial wall, and a second radial wall. At least one of the radial walls may be substantially more rigid than the circumferential walls. Additionally, the radial walls and the circumferential walls of the collection lumens may be constructed and arranged such that the collection array could be extended and/or collapsed into predefined shapes.

The distal end of the collection array could function as a plurality of collection ports, each collection port being in fluid communication with at least one collection lumen. In one embodiment of the present invention, at least one of the collection ports may be directed axially, facing either distally or proximally. In an alternate embodiment, at least one of the collection ports may be directed radially.

The proximal end of the collection array could function as a plurality of retrieval ports, each retrieval port being in fluid communication with at least one collection lumen. The retrieval ports may be fluidly coupled to a suction means, such as a vacuum source, for extracting thrombi, debris, urged core material, etc., from the lumen of the blood vessel. The collection array may be constructed and arranged to minimize occlusion of the collection lumens.

A method in accordance with one embodiment may include the steps of inserting the distal end of the catheter of the present invention into a lumen of the blood vessel, positioning the collection ports proximate one or more plaque deposits, extending the collection array to engage the inner wall of the blood vessel and/or the one or more plaque deposits, rupturing the one or more plaque deposits and urging the core material therefrom, drawing the urged core material, thrombi, debris, etc., into the collection array through the collection ports by fluidly connecting a suction means to the retrieval ports of the collection array, and extracting the urged core material, thrombi, debris, etc., from the lumen of the blood vessel.

DETAILED DESCRIPTION OF THE INVENTION

The following detailed description should be read with reference to the drawings, in which like elements in different drawings are numbered in like fashion. The drawings are diagrammatic in nature. Those skilled in the art will recognize that many of the embodiments described herein may have suitable alternatives that could be utilized without deviating from the scope, intent, and spirit of the invention.

Figure 1:
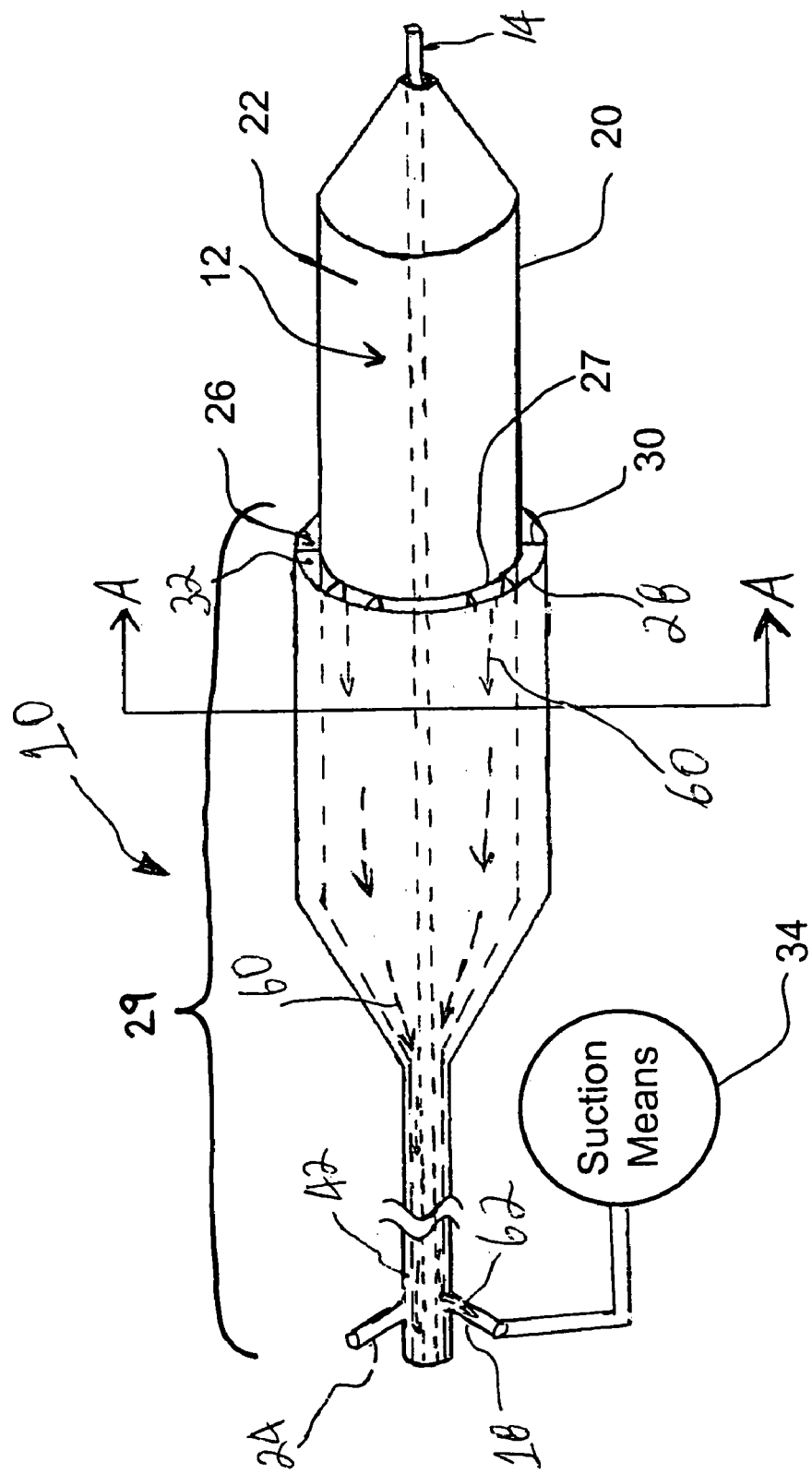
FIG. 1 is a schematic of a catheter in accordance with an embodiment of the present invention.

FIG. 1 is a schematic of catheter 10 with distally oriented collection ports 32 in accordance with an embodiment of the present invention. Catheter 10 may include elongated shaft 12 having a distal end and a proximal end. Balloon 20 is disposed about a portion of elongated shaft 12 proximate the distal end thereof.

In accordance with an embodiment of the present invention, catheter 10 includes a collection array having a plurality of collection lumens 26 around balloon 20. Each collection lumen 26 could be defined by first circumferential wall 27, second circumferential wall 28, and a plurality of radial walls 30. In one embodiment, at least one of the radial walls 30 may be substantially more rigid than both first and second circumferential walls 27 and 28, respectively. In another embodiment, all radial walls 30 could be substantially more rigid than both first and second circumferential walls 27 and 28, respectively. In use, the rigidity of radial walls 30 could aid in rupturing the one or more plaque deposits when the collection array 29 is extended, and may also reduce the likelihood of occluding collection lumens 26 when extracting thrombi, debris, core material urged from the one or more ruptured plaque deposits, etc., from the lumen of the blood vessel.

The distal end of the collection array 29 may consist of a plurality of collection ports 32, each collection port being in fluid communication with at least one collection lumen 26. Additionally, the proximal end of the collection array 29 may consist of retrieval port 18 fluidly coupled to suction means 34, such as a vacuum source, to enable extraction of thrombi, debris, urged core material, etc., from the lumen of the blood vessel. In use, thrombi, debris, core material, etc., entering collection lumens 26 through collection ports 32 could travel along flow paths 60 within the collection array 29 and extracted through retrieval port 18 along path 62.

The collection array 29 may have a contracted position in which collection lumens 26 are somewhat collapsed, and an expanded position in which collection lumens 26 are extended and substantially unobstructed. In one embodiment, collection lumens 26 could be radially extended or collapsed, respectively, by inflating or deflating balloon 20. Balloon wall 22, defining an outer extent of balloon 20, may engage first circumferential wall 27 when balloon 20 is inflated. Collection lumens 26 could then be extended upon further inflating balloon 20. Balloon wall 22 may be retracted and disengaged from first circumferential wall 27 by deflating balloon 20. The collection array 29 could be designed and constructed such that collection lumens 26 may collapse when balloon wall 22 disengages from first circumferential wall 27. In an alternate embodiment, the collection array could be radially expanded or contracted by a mechanical means, such as a plurality of resilient arms.

In accordance with designs and methods of use of intravascular catheters, elongated shaft 12 may also include lumen 42 for inflating and/or deflating balloon 20 through port 24, as is well known in the art. Additionally, elongated shaft 12 could include guidewire lumen 14 therethrough. A fluid source may be coupled to port 24 at the proximal end of lumen 42. The distal portion of lumen 42 may be in fluid communication with balloon 20 through an orifice such that lumen 42 may be used for injecting and/or removing fluids from balloon 20, as is well known in the art, for the purpose of inflating and/or deflating balloon 20.

Figure 2:
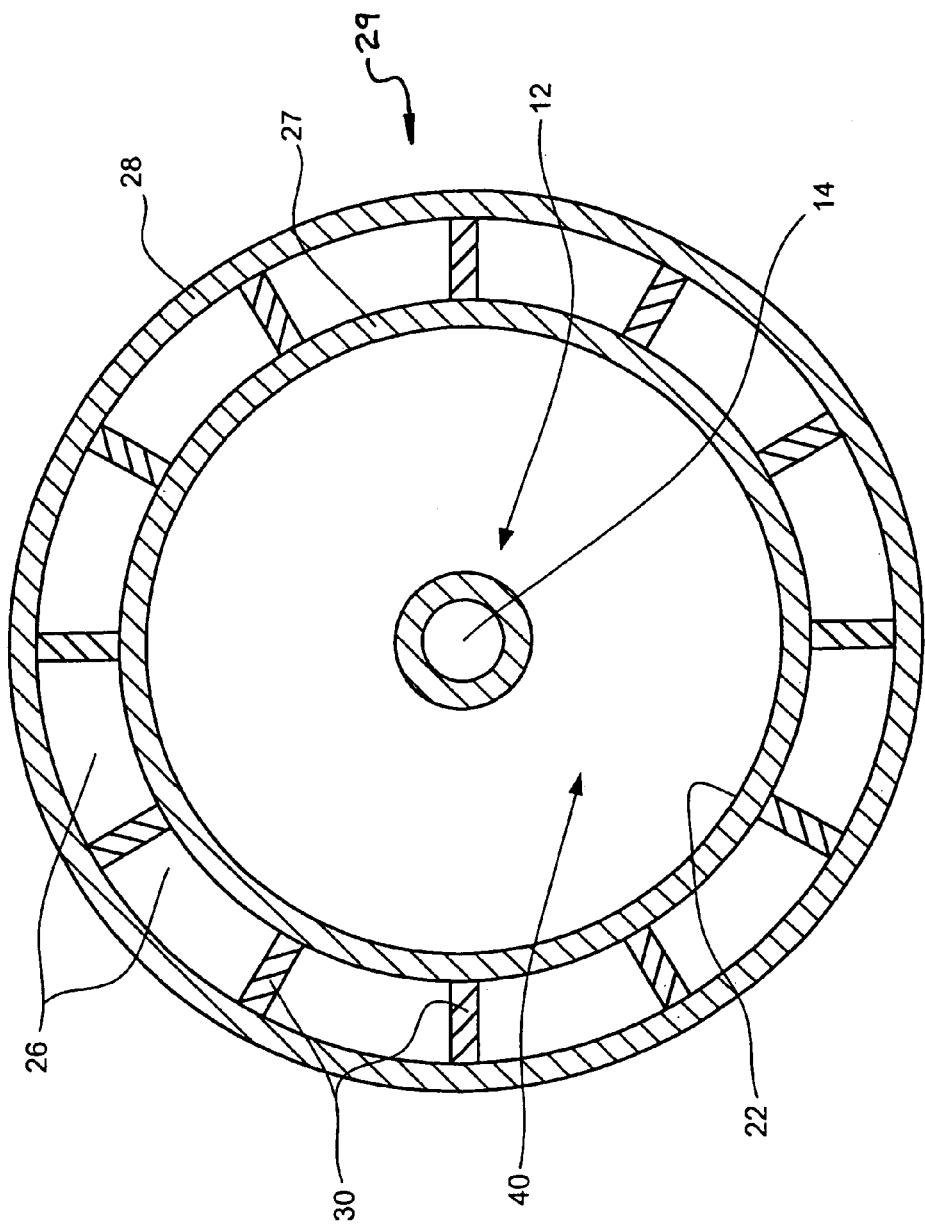
FIG. 2 is a view of cross-section A—A of the catheter of FIG. 1.

FIG. 2 is a schematic of cross-section A—A showing the fully extended collection array of FIG. 1, proximate the distal ends of collection lumens 26. Like elements in FIGS. 1 and 2, are numbered in like fashion. In FIG. 2, element 40 represents the chamber of balloon 20 encompassed by balloon wall 22 engaged with the inner surface of first circumferential wall 27.

Figure 3:
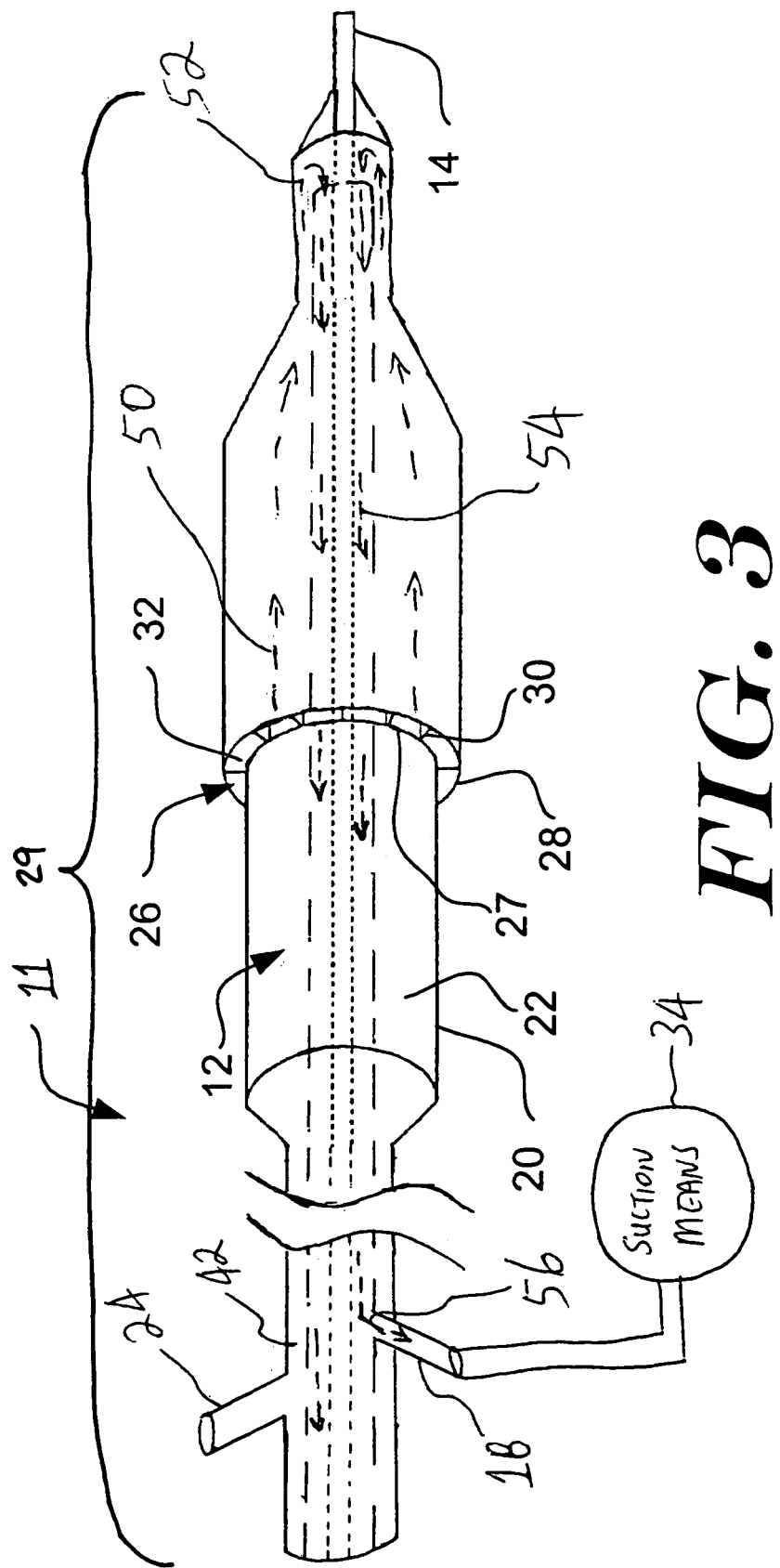
FIG. 3 is a schematic of a catheter in accordance with another embodiment of the present invention.

FIG. 3 is a schematic of catheter 11 with proximally oriented collection ports 32 in accordance with another embodiment of the present invention. Except for the direction in which collection ports 32 face, and the flow direction of material through the collection array 29, catheter 11 of FIG. 3 is substantially similar to the above described catheter 10 of FIG. 1. Therefore, a detailed description for catheter 11 of FIG. 3 is not repeated. In use, thrombi, debris, core material, etc., entering collection lumens 26 through collection ports 32 could first travel within the collection array 29 along flow paths 50 towards the distal end of catheter 11. Proximate the distal end of catheter 11, the collection array 29 may turn 180 degrees towards the proximal end of catheter 11, causing a change in flow direction therein as illustrated by flow paths 52. Thereafter, thrombi, debris, core material, etc., within the collection array 29 could travel along path 54 towards the proximal end of catheter 11, and subsequently get extracted through retrieval port 18 along path 56.

Figure 4:
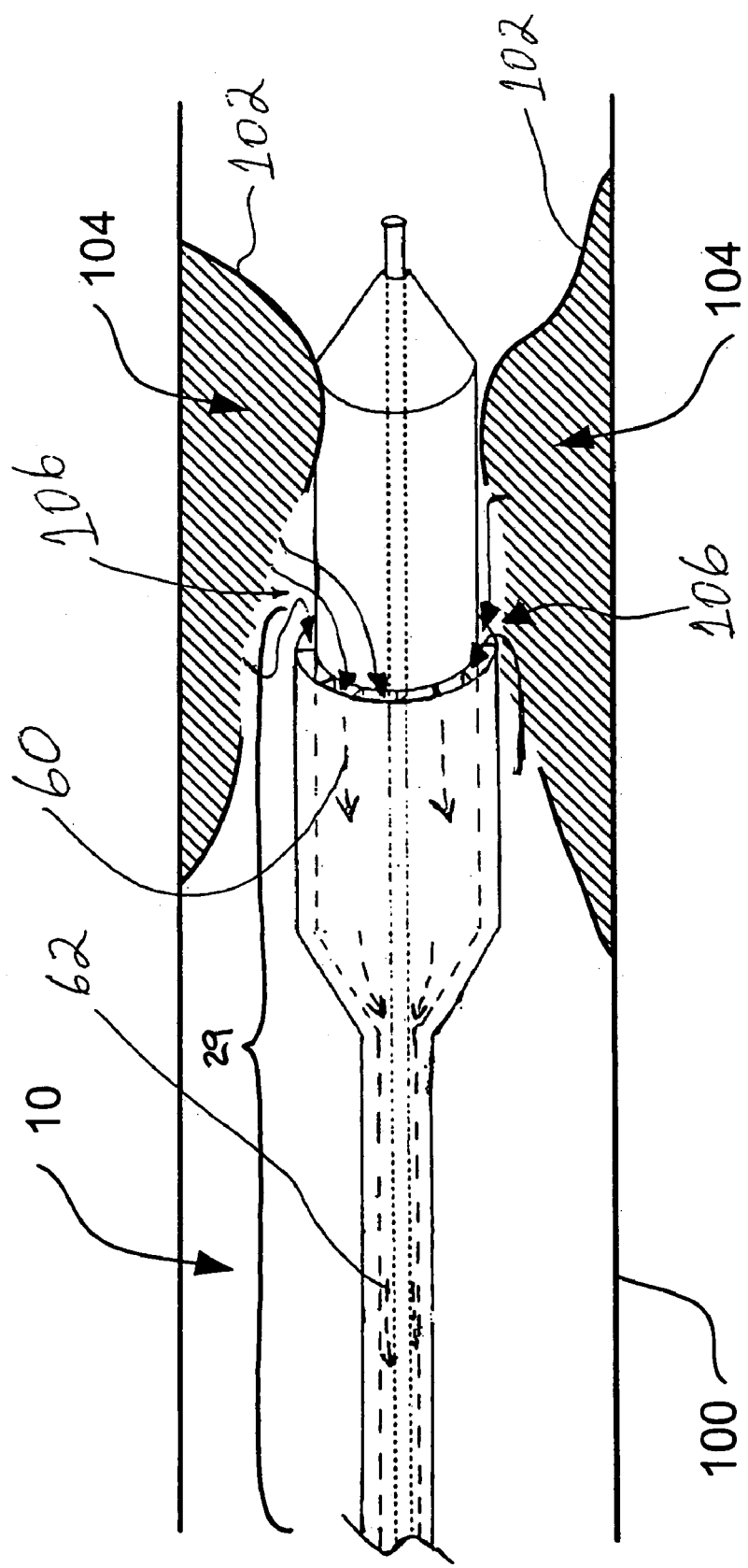
FIG. 4 is an illustration of extracting the core material by a method of the present invention using the catheter of FIG. 1.

FIG. 4 is an illustration of a method for extracting thrombi, debris, core material urged from one or more ruptured plaque deposits, etc., from the lumen of blood vessel 100 using catheter 10 of FIG. 1 with distally oriented collection ports. Plaque deposits 102, having core material 104, are shown attached to the inner wall of the lumen of blood vessel 100. The distal portion of catheter 10 is shown disposed proximate one or more plaque deposits 102 within blood vessel 100.

In one embodiment of a method for removing one or more plaque deposits 102, the distal portion of catheter 10 may be inserted into the lumen of blood vessel 100 and collection ports 32 positioned proximate the one or more plaque deposits 102. One of numerous means, such as, inflating balloon 20 using methods well known in the art, mechanical means such as a plurality of resilient arms, etc., could be used to extend the collection array 29. When fully extended, balloon wall 22 and/or second circumferential wall 28 of collection lumens 26 could engage the inner wall of blood vessel 100 and/or the one or more plaque deposits 102. The distal portion of catheter 10 may then be manipulated to rupture the one or more plaque deposits 102. Core material 104 urged from the one or more ruptured plaque deposits 102 could be extracted from the lumen of blood vessel 100 by fluidly connecting a suction means 34 to retrieval ports 18 at the proximal end of the collection array 29. Urged core material 104 may be drawn along flow paths 106 into collection lumens 26 through the one or more collection ports 32. In some instances, the presence of core material 104 within blood vessel 100 may cause thrombi to form. Additionally, the process of rupturing the one or more plaque deposits 102 could release debris within the lumen of blood vessel 100. Such thrombi, debris, etc., proximate of collection ports 32 may also be drawn along flow paths 106 into the collection array 29 and extracted from the lumen of blood vessel 100 by suction means 34.

Figure 5:
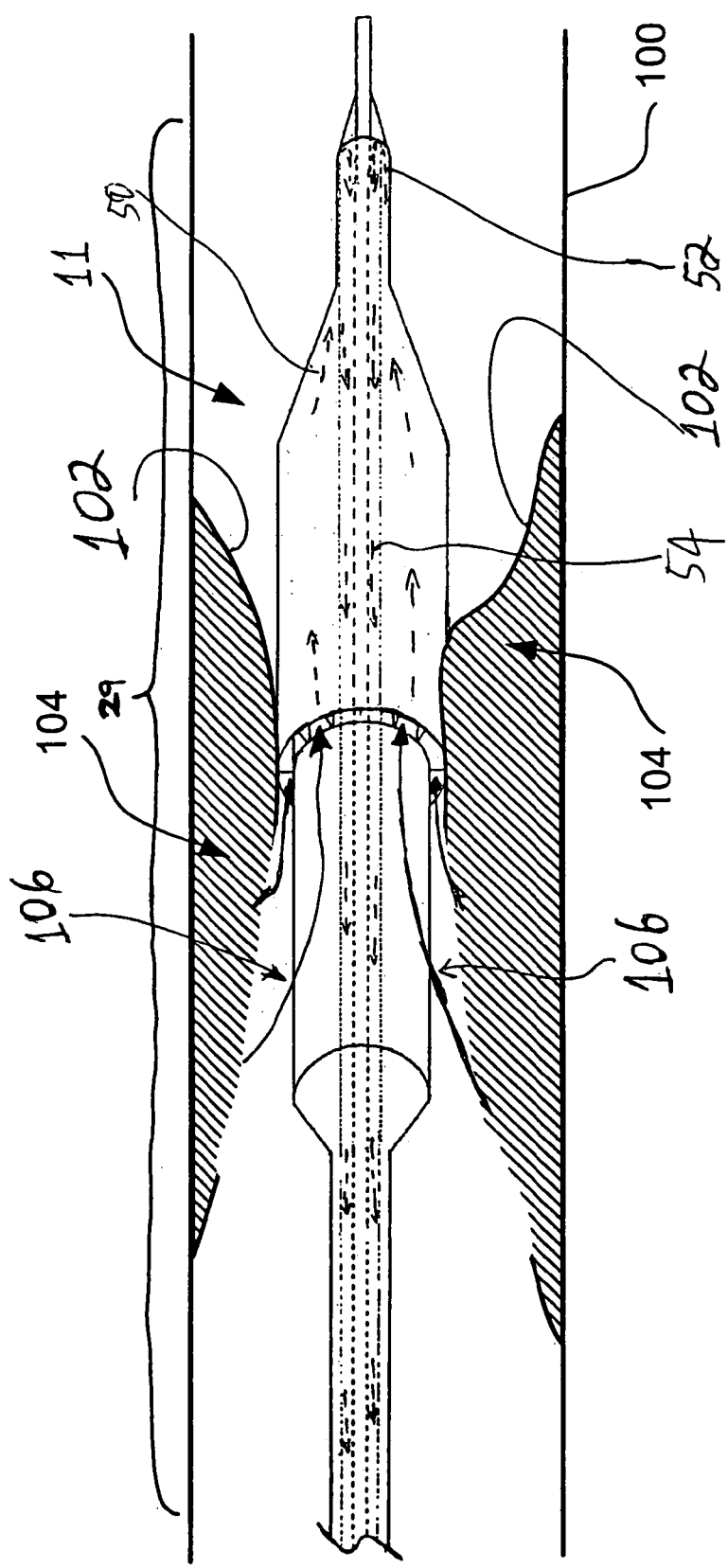
FIG. 5 is an illustration of extracting the core material by a method of the present invention using the catheter of FIG. 3.

FIG. 5 is an illustration of a method for extracting thrombi, debris, core material urged from one or more ruptured plaque deposits, etc., from the lumen of a blood vessel using catheter 11 of FIG. 3 with proximally oriented collection ports. Except for the direction in which collection ports 32 face, and the associated direction of collection lumens 26 and flows paths 106, the extraction method shown in FIG. 5 is substantially similar to the extraction method described in association with FIG. 4. Therefore, a detailed description for the method illustrated in FIG. 5 is not provided.

It should be understood that this disclosure is, in many respects, only illustrative. Changes may be made for example, in details, particularly in matters of shape, size, and arrangement of parts without exceeding the scope of the invention.

What is claimed is:

1. A catheter for removing core material from one or more plaque deposits on an inside wall of a blood vessel, said catheter comprising:
   an elongate shaft having a proximal end and a distal end; and
   a radially extendible collection array disposed about a portion of the elongate shaft and near the distal end of the elongated shaft, the radially extendible collection array having one or more collection lumens open to the blood vessel to receive the core material at the periphery of the blood vessel, remove the core material from the blood vessel, and maintain the core material out of the blood vessel,
   wherein each collection lumen is defined, at least in part, by a first circumferential wall, a second circumferential wall, a first radial wall, and a second radial wall.

2. The catheter of claim 1 further comprising a retrieval port near the proximal end of the elongate shaft and a suction means fluidly coupled to the retrieval port.

3. The catheter of claim 1, wherein the collection array is radially extendible and radially collapsible.

4. The catheter of claim 1 further comprising means for radially extending and/or radially collapsing the collection array.

5. The catheter of claim 4, wherein the means for radially extending and/or radially collapsing the collection array includes a hydraulic mechanism.

6. The catheter of claim 5, wherein the hydraulic mechanism comprises a balloon, said balloon having an inflated state and a deflated state.

7. The catheter of claim 4, wherein the means for radially extending and/or radially collapsing the collection array includes a mechanical mechanism.

8. The catheter of claim 1, wherein for each collection lumen, said first and second radial walls are disposed between said first and second circumferential walls.

9. The catheter of claim 1, wherein at least one of the radial walls is substantially more rigid than said first and second circumferential walls.

10. The catheter of claim 1, wherein the first circumferential wall defines, at least in part, an outer surface of a balloon.

11. The catheter of claim 1, wherein said first and second circumferential walls and said first and second radial walls are constructed and arranged such that the collection array is collapsible into a predefined shape.

12. The catheter of claim 1, wherein the distal end of each of the one or more collection lumens comprises a collection port.

13. The catheter of claim 12, wherein at least one collection port is fluidly connectible to a suction means.

14. The catheter of claim 12, wherein at least one collection port is directed substantially axially.

15. The catheter of claim 14, wherein the at least one axially-directed collection port is directed away from the proximal end of the elongate shaft.

16. The catheter of claim 14, wherein the at least one axially-directed collection port is directed toward the proximal end of the elongate shaft.

17. The catheter of claim 12, wherein at least one collection port is directed radially.

18. The catheter of claim 12, further comprising a retrieval port near the proximal end of the elongate shaft, wherein at least one collection lumen provides fluid communication between the retrieval port and at least one collection port.

19. The catheter of claim 12, further comprising one or more retrieval ports near the proximal end of the elongate shaft, wherein the one or more retrieval ports correspond to the one or more collection lumens.

20. The catheter of claim 1, wherein an outer circumferential wall of the collection array defines, at least in part, an outer extent of an engagement surface for:
   engaging the inner wall of the blood vessel and the one or more plaque deposits;
   rupturing the one or more plaque deposits in one or more locations; and
   urging core material from the one or more ruptured plaque deposits.

* * * * *